United States Patent [19]
Jung
[11] Patent Number: 4,802,472
[45] Date of Patent: Feb. 7, 1989

[54] EMERGENCY AIR SUPPLY DEVICE

[76] Inventor: Sakun J. Jung, 325 Hammonton Pl., Silver Spring, Md. 20904

[21] Appl. No.: 105,617

[22] Filed: Oct. 8, 1987

[51] Int. Cl.[4] ............ A61M 16/00

[52] U.S. Cl. ............ 128/204.18; 128/205.24; 128/206.21; 128/207.12

[58] Field of Search ............ 128/204.18, 205.24, 128/205.25, 206.21, 206.28, 207.12, 201.28, 205.22; 137/205.13

[56] References Cited

U.S. PATENT DOCUMENTS

| | | | |
|---|---|---|---|
| D. 143,084 | 12/1945 | Littlefield et al. | 29/6 |
| D. 251,622 | 4/1979 | Garrison et al. | 29/6 |
| D. 283,742 | 5/1986 | Hall | 29/6 |
| 2,733,042 | 1/1956 | Culbertson | 128/205.24 |
| 2,931,357 | 4/1960 | Arborelius et al. | 128/204.28 |
| 4,233,970 | 11/1980 | Kranz | 128/205.24 |
| 4,565,196 | 1/1986 | Melby et al. | 128/205.25 |

*Primary Examiner*—Edward M. Coven
*Assistant Examiner*—J. P. Lacyk
*Attorney, Agent, or Firm*—Birch, Stewart, Kolasch, & Birch

[57] ABSTRACT

An air supply device which may be used for emergencies such as an escape from a buring building comprises an air tank having a hose connected to a face mask and an activation element and a regulation element. The activation element consists of a spring biased valve which will automatically move to an opened position when a holding pin is released. The regulation element consists of a U-shaped valve having a first end for covering apertures leading to the hose and a second end in engagement with an expansion element. As air is removed from the tank during use of the device, the expansion element will expand due to a decrease in air pressure within the tank. As the expansion element enlarges, the U-shaped valve will move so as to expose additional apertures. A constant supply of air is therefore easily and automatically maintained.

10 Claims, 2 Drawing Sheets

EMERGENCY AIR SUPPLY DEVICE

BACKGROUND OF THE INVENTION

1. Field of the Invention

The present invention relates to an air supply device for use in emergency situations such as fires or the like. This air supply device consists of a tank with a hose connected to a face mask, an activation means and an automatic regulation means.

2. Description of the Background Art

Various air supply devices are known in the prior art. However, these air supply devices have been expensive to manufacture and to maintain. Accordingly, as costs are generally high, it is economically prohibitive to store these devices in hotel rooms, offices, high rise buildings or the like for use in emergency situations. Furthermore, as these devices are generally complicated, not only will the cost of these devices be high, but their reliability, especially in emergency situations, may be reduced. For instance, an operator may be on the verge of panic if he or she is involved in a fire and therefore be unable to carry out complicated procedures. Furthermore, the need for maintenance of these prior art devices is relatively high.

Accordingly, a need exists in the art for a simple and effective emergency air supply which is inexpensive to manufacture and requires little maintenance. Furthermore, there is a need in the art for an emergency air supply which is easy to activate and which will operate automatically.

SUMMARY OF THE INVENTION

Accordingly, it is the primary object of the invention to provide an emergency air supply which is inexpensive to manufacture.

It is another object of the present invention to provide an emergency air supply which requires limited maintenance.

It is still another object of the present invention to provide an emergency supply which is relatively compact and easy to store.

It is yet another object of the present invention to provide an emergency air supply which is automatic in operations such that no complicated operator control is needed, even in emergency situations.

These and other objects of the present invention are fulfilled by providing an air supply device comprising, a tank for holding air, said tank having an outlet therein and activation means for permitting release of air from the tank through said outlet therein. The activation means comprises a movable blocking element for closing said outlet therein, said blocking element being movable from a closed position wherein the outlet is closed to an open position wherein the outlet is opened and wherein release of air from the tank is permitted, means for urging said blocking element from said closed position to said opened position, and means for holding said blocking element in the closed position. The means for holding is removable such that said means for urging is permitted to move said blocking element to said opened position to permit the release of air. The device of the invention also comprises regulation means for regulating the flow of air from the tank during said release of air, said regulation means comprising, an element connected to said outlet, said element having a plurality of ports therein such that the air in the tank is in communication with said outlet, movable valve means for opening and closing a plurality of said ports, means for urging said valve means to a position closing a majority of said ports, and expansion means for overcoming said means for urging in order to move said valve means to various positions wherein successively more ports are opened. The expansion means is responsive to the pressure of air in the tank such that as air is removed from the tank, said valve is moved to open more ports in order to maintain a substantially constant flow of air.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
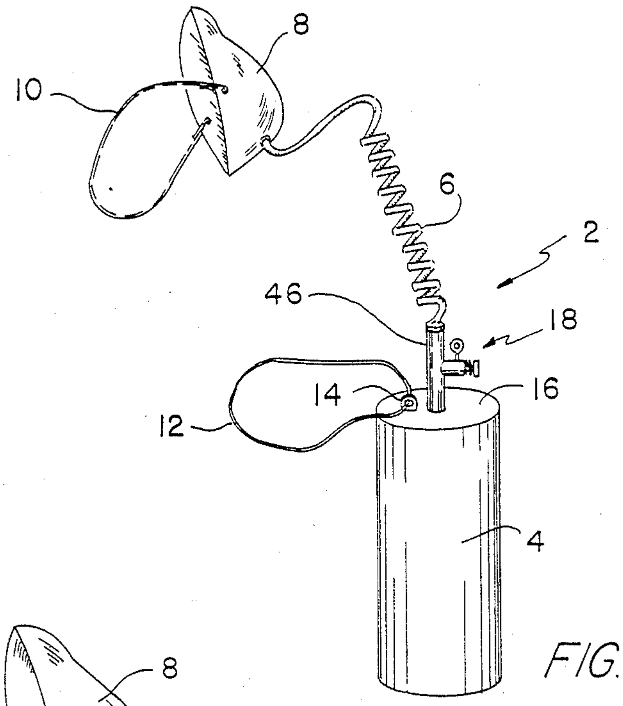
FIG. 1 is a perspective view of the air supply device of the present invention.

Referring in detail to the drawings and with particular reference to FIG. 1, an air supply device 2 is shown. This device is contemplated for use in hotels or office buildings or other such structures and is for use during "emergency-type situations". For instance, these devices may be used to escape a burning building. The device of the present invention may additionally be used for personal use, such as in the home or whenever an ensured supply of air is needed.

The device of the present invention comprises an air tank 4 with a connection hose 6 attached thereto. This hose is attached to a hose attachment element 46 located at the top 16 of air tank 4. On the opposite end of hose 6 is a face mask 8. This face mask has an optional head strap 10 which may be placed around the head of a user in order to ensure that the face mask remains in place.

The air tank 4 of the present invention also has a carrying strap 12 which is connected to the top 16 of the tank by a strap connector 14. This strap is optional and merely facilitates carrying of the air tank 4.

The air tank 4 is initially filled with compressed air or another suitable gas. Any gas which is suitable for a user of the device to breathe can be employed. While the gas in the tank will be referred to as "air" throughout the specification, it should be kept in mind that other suitable gases, such as pure oxygen, may be used.

Figure 2:
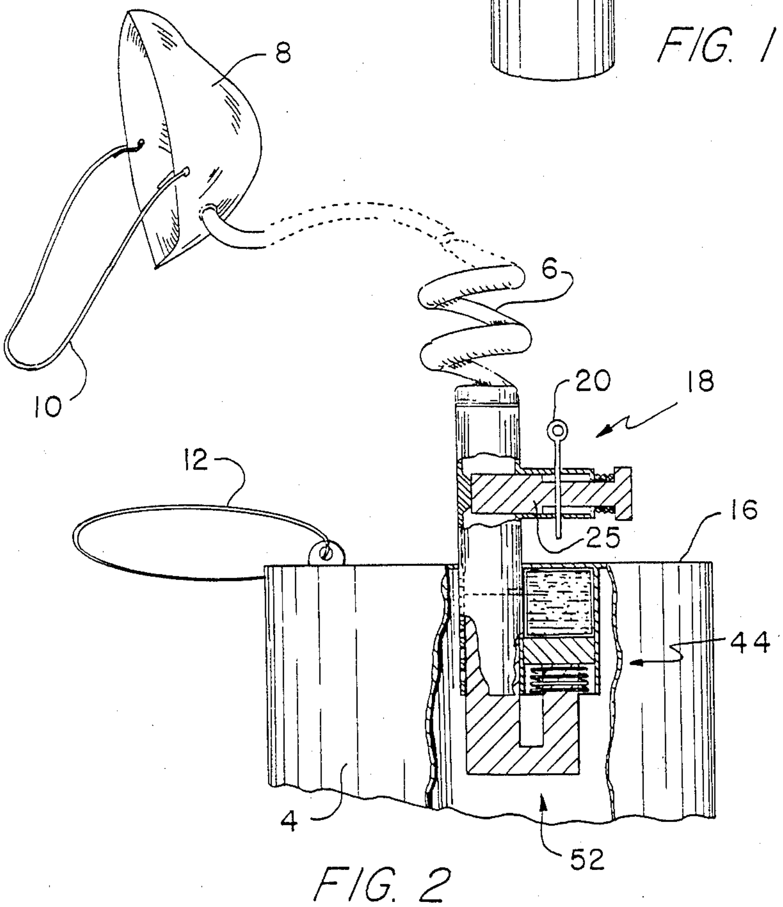
FIG. 2 is a cross-sectional view of a portion of the air supply device shown in FIG. 1.
Figure 3:
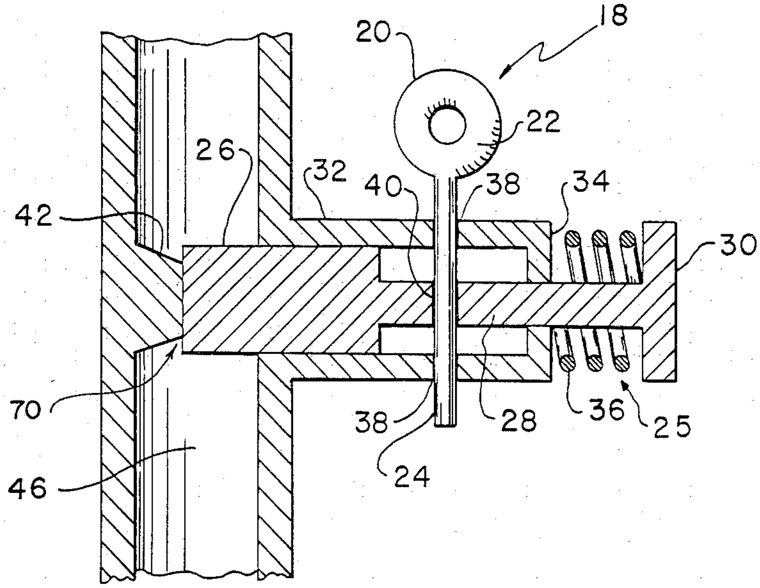
FIG. 3 is a cross-sectional view of the activation means of the invention.

Now referring in detail to FIG. 2, the air supply device of the instant invention is shown with an activation means 18 and a regulation means 44. In particular, the activation means 18 is affixed to a portion of the hose attachment element 46 outside of tank 4. Referring to FIGS. 2 and 3, this activation means 18 includes a release pin 20. This release pin 20 has a gripping end 22 and a distal end 24. Also included in the activation means is an activation valve 25. This valve 25 consists of a hose blocking end 26, a shank 28 and an activation valve head 30. Hose blocking end 26 extends into hose attachment element 46 and blocks the passage of air therethrough. An abutment portion 42 is further provided for engagement with blocking end 26 in order to insure a proper seal and to prevent the escape of air from tank 4.

The hose blocking end 26 and a portion of shank 28 of valve 25 are enclosed in a housing 32. This housing 32 has an end 34 which is an engagement with an end portion of activation spring 36. Spring 36 extends between housing end 34 and valve head 30. This spring 36 urges valve 25 to the opened position.

Initially, the activation means 18 is set by inserting release pin 20 through housing aperture 38 and shank aperture 40 in order to lock the activation valve 25 in the closed position shown in FIG. 3. However, upon removal of pin 20, the activation spring 36 will cause the valve 25 to move to the right as seen in FIG. 3. This movement will cause hose blocking end 26 to disengage from abutment portion 42 and permit passage of air through an outlet indicated at 70 and into connection hose 6. Thus, a flow of air may then occur between tank 4 and face mask 8.

Figure 4:
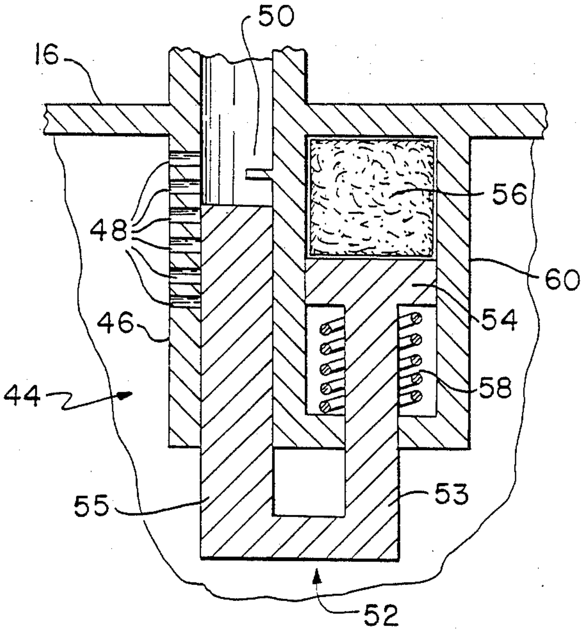
FIG. 4 is a cross-sectional view of the regulation means of the invention.

In order to regulate this flow of air, a regulation means 44 is provided. Referring to FIGS. 2 and 4, regulation means 44 includes the lower portion of hose attachment element 46. This element 46 has several apertures 48 therein. While these apertures are shown as a single row of longitudinally aligned apertures in FIG. 4, it is contemplated that other arrangements of apertures may be used. In other words, a plurality of rows of apertures may be used or a series of apertures which encircle the length of the attachment element 46 may be used. Nonetheless, these apertures provide for regulation of the flow of air in conjunction with a regulation valve 52.

This regulation valve 52 comprises a U-shaped regulation valve stem 53 and a regulation valve head 54. The end portion 55 of stem 53 is inserted into the attachment element 46. This end portion 55 is capable of longitudinally reciprocating along the length of this attachment element 46. A stop member 50 is provided to prevent upward movement of the end portion 55 beyond a predetermined position.

The other end of the regulation valve 52 contains valve head 54. This valve head 54 is in engagement with a regulation spring 58. Also, the opposite end of this valve head 54 is in engagement with an expansion element 56. This element 56 and spring 58 along with valve head 54 are contained within expansion element housing 60.

The expansion element 56 consists of a flexible bag or the like which is filled with a pressurized gas. This pressurized gas exerts a downward force on valve head 54. The valve head 54 is normally urged upwardly by regulation spring 58. This movement causes the lower apertures 48 in attachment element 46 to be closed by the end 53 of U-shaped valve 52 as the upward force of spring 58 is initially sufficient to overcome the downward force of the pressurized gas in expansion element 56.

In operation, the release pin 20 is removed from activation means 18. This removal causes activation valve 25 to move to the right as seen in FIG. 3. A flow of air may then commence through hose 6 to face mask 8. The exposed upper aperture 48 permits air to pass through hose attachment element 46 to hose 6. Initially, a majority of these apertures 48 are closed by the end 55 of U-shaped valve 52. However, as air is removed from tank 4, the internal pressure of this tank will decrease. This decrease in internal pressure will enable the gas within expansion element 56 to expand this element. Such expansion will cause valve head 54 to move downwardly. This downward movement will result in additional apertures 48 being exposed. As these apertures are exposed, air may more easily exit tank 4. Thus, when there is a high internal pressure initially in tank 4, only a small number of apertures 48 need be exposed. However, as this internal pressure within tank 4 decreases, additional apertures 48 are exposed in order to ensure a constant supply of air through hose 6 to mask 8.

While various references to "right", "left", "up", and "down" have been made in the specification, such terms are merely for reference to the attached drawings. Thus, various modifications which are within the spirit and scope of the present invention are contemplated for the air supply device. For instance, this device may omit the use of a face mask 8 or the activation means 18 may be located within tank 4.

The simple construction and design of the present invention yields an effective air supply device which is inexpensive to manufacture, thus increasing acceptance thereof. This device may be readily used in hotels, commercial offices or even within private homes. Since the device of the present invention is relatively simple in construction, maintenance thereof is also reduced.

The device of the present invention further has the benefit of automatic control. Thus, in "panic situations" when an operator may be unable to perform complicated tasks, the device of the instant invention would not only be adequate but would be preferable. An operator of the device of the present invention merely needs to remove release pin 20 in order to ensure a constant supply of air to mask 8. Reliability of the device is therefore increased.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. An air supply device comprising:

a tank for holding air, said tank having an outlet therein;

activation means for permitting release of said air from said tank through said outlet, said activation means comprising, a movable blocking element for closing said outlet, said blocking element being movable from a closed position wherein said outlet is closed to an open position wherein said outlet is opened and wherein release of air from said tank is permitted, means for urging said blocking element from said closed position to said opened position, and means for holding said blocking element in the closed position, said means for holding being removable such that said means for urging is permitted to move said blocking element to said opened position to permit said release of air;

regulation means for regulating the flow of air from said tank during said release of air, said regulation means comprising, a hollow element connected to said outlet, said element having a plurality of generally, longitudinally aligned ports therein such that said air in said tank is in communication with said outlet, movable valve means for opening and closing a plurality of said ports, said movable valve means comprising a U-shaped valve stem having an end portion enclosed by said hollow element, said end portion of said valve stem being reciprocable to sequentially open and close said plurality of generally, longitudinally aligned ports, means for urging said valve means to a position closing a majority of said ports, and expansion means for overcoming said means for urging in order to move said valve means to various positions wherein successively more ports are opened, said expansion means being responsive to pressure of said air in said tank such that as air is removed form the tank, said valve means is moved to open more ports in order to maintain a substantially constant flow of air; and means for furnishing air to a user from said tank when said activation means permits release of said air.

2. The air supply device of claim 1, wherein said means for urging said valve means comprises a spring.

3. The air supply device of claim 1, wherein said means for urging said blocking element comprises a spring.

4. The air supply device of claim 1, wherein said means for holding comprises a pin and wherein a portion of said movable blocking element is enclosed within a housing, said housing and said blocking element each having an aperture therein to receive said pin such that said blocking element will be locked in said closed position when said pin is received in said apertures and such that said means for urging will be permitted to move said blocking element to said opened position when said pin is removed from said apertures.

5. The air supply of claim 1, wherein said means for furnishing air further comprises:

a hose connected to said outlet for receiving discharged air from said tank; and a face mask connected to said hose, said face mask receiving said discharged air from said hose and permitting the user of said device to breathe said discharged air.

6. An air supply device comprising:

a tank for holding air, said tank having an outlet therein;

activation means for permitting release of said air from said tank through said outlet, said activation means comprising, a movable blocking element for closing said outlet, said blocking element being movable from a closed position wherein said outlet is closed to an open position wherein said outlet is opened and wherein release of air from said tank is permitted, means for urging said blocking element from said closed position to said opened position, and means for holding said blocking element in the closed position, said means for holding being removable such that said means for urging is permitted to move said blocking element to said opened position to permit said release of air;

regulation means for regulating the flow of air from said tank during said release of air, said regulation means comprising:

a hollow element connected to said outlet, said hollow element having a plurality of ports therein such that said air in said tank is in communication with said outlet, movable valve means for opening and closing a plurality of said ports, means for urging said valve means to a position closing a majority of said ports, and expansion means for overcoming said means for urging in order to move said valve means to various positions therein successively more ports are opened, said expansion means being responsive to pressure of said air in said tank such that as air is removed from the tank, said valve means is moved to open more ports in order to maintain a substantially constant flow of air, said expansion means including a flexible container with pressurized gas therein, said container and said tank each having an internal pressure, said pressure of said container being selected so as to be responsive to said pressure in said tank such that withdrawal of said air from said tank causes said internal pressure within said tank to decrease and said container to expand in response thereto, the expansion of said container causing said movable valve means to open additional ports and to thereby maintain said substantially constant flow of air; and means for furnishing air to a user from said tank when said activation means permits release of said air.

7. The air supply device of claim 6, wherein said means for urging said valve means comprises a spring.

8. The air supply device of claim 6, wherein said means for urging said blocking element comprises a spring.

9. The air supply device of claim 6, wherein said means for holding comprises a pin and wherein a portion of said movable blocking element is enclosed within a housing, said housing and said blocking element each having an aperture therein to receive said pin such that said blocking element will be locked in said closed position when said pin is received in said apertures and such that said means for urging will be permitted to move said blocking element to said opened position when said pin is removed from said apertures.

10. The air supply device of claim 6, wherein said means for furnishing air further comprises:

a hose connected to said outlet for receiving discharged air from said tank; and a face mask connected to said hose, said face mask receiving said discharged air from said hose and permitting the user of said device to breathe said discharged air.

* * * * *